(12) United States Patent
Rottenberg et al.

(10) Patent No.: US 10,564,362 B2
(45) Date of Patent: Feb. 18, 2020

(54) LIGHT COUPLER WITH MICROSTRUCTURES ASYMMETRICALLY DISTRIBUTED ALONG LONGITUDINAL AXIS

(71) Applicant: IMEC VZW, Leuven (BE)

(72) Inventors: Xavier Rottenberg, Kessel-Lo (BE); Tom Claes, Merelbeke (BE); Dries Vercruysse, Sint-Andries (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/538,926

(22) PCT Filed: Dec. 28, 2015

(86) PCT No.: PCT/EP2015/081304
§ 371 (c)(1),
(2) Date: Jun. 22, 2017

(87) PCT Pub. No.: WO2016/107851
PCT Pub. Date: Jul. 7, 2016

(65) Prior Publication Data
US 2017/0351035 A1 Dec. 7, 2017

(30) Foreign Application Priority Data
Dec. 29, 2014 (EP) .................................... 14200427

(51) Int. Cl.
*G02B 6/34* (2006.01)
*G01N 15/14* (2006.01)
(Continued)

(52) U.S. Cl.
CPC ........... *G02B 6/34* (2013.01); *G01N 15/1434* (2013.01); *G01N 15/1456* (2013.01);
(Continued)

(58) Field of Classification Search
None
See application file for complete search history.

(56) References Cited

U.S. PATENT DOCUMENTS

| 5,033,812 A | * | 7/1991 | Yoshida | G02B 6/124 |
| | | | | 385/37 |
| 5,420,947 A | * | 5/1995 | Li | G02B 6/34 |
| | | | | 359/569 |

(Continued)

FOREIGN PATENT DOCUMENTS

| FR | 2893414 A1 | 5/2007 |
| WO | 2013/179023 A1 | 12/2013 |

(Continued)

OTHER PUBLICATIONS

PCT International Search Report and Written Opinion, PCT International Application No. PCT/EP2015/081304, dated Apr. 19, 2016, 10 pages.

*Primary Examiner* — Andrew Jordan
(74) *Attorney, Agent, or Firm* — McDonnell Boehnen Hulbert & Berghoff LLP

(57) ABSTRACT

Embodiments described herein relate to a light coupler, a photonic integrated circuit, and a method for manufacturing a light coupler. The light coupler is for optically coupling to an integrated waveguide and for out-coupling a light signal propagating in the integrated waveguide into free space. The light coupler includes a plurality of microstructures. The plurality of microstructures is adapted in shape and position to compensate decay of the light signal when propagating in the light coupler. The plurality of microstructures is also adapted in shape and position to provide a power distribution of the light signal when coupled into free space such that the power distribution corresponds to a predetermined target power distribution. Each of the microstructures forms an optical scattering center. The microstructures are posi- (Continued)

tioned on the light coupler in accordance with a non-uniform number density distribution.

20 Claims, 14 Drawing Sheets

(51) Int. Cl.
    *G02B 27/22* (2018.01)
    *G01N 15/00* (2006.01)
    *G01N 15/10* (2006.01)

(52) U.S. Cl.
    CPC ..... *G01N 15/1484* (2013.01); *G02B 27/2292* (2013.01); *G01N 2015/0065* (2013.01); *G01N 2015/1006* (2013.01); *G01N 2015/144* (2013.01); *G01N 2015/149* (2013.01)

(56) References Cited

U.S. PATENT DOCUMENTS

| | | | | |
|---|---|---|---|---|
| 5,625,729 | A * | 4/1997 | Brown | G02B 6/34 359/573 |
| 5,835,643 | A * | 11/1998 | Fukumoto | G02B 6/34 385/7 |
| 6,640,034 | B1 * | 10/2003 | Charlton | B82Y 20/00 385/122 |
| 7,006,732 | B2 * | 2/2006 | Gunn, III | G02B 6/1228 359/629 |
| 7,065,272 | B2 * | 6/2006 | Taillaert | B82Y 20/00 359/563 |
| 7,184,625 | B2 * | 2/2007 | Gunn, III | G02B 6/12004 372/6 |
| 7,245,803 | B2 * | 7/2007 | Gunn, III | G02B 6/1228 359/574 |
| 7,298,945 | B2 * | 11/2007 | Gunn, III | G02B 6/1228 359/629 |
| 7,397,987 | B2 * | 7/2008 | Witzens | G02B 6/124 385/14 |
| 9,103,975 | B2 * | 8/2015 | Yu | G02B 6/124 |
| 9,128,226 | B2 * | 9/2015 | Fattal | G02B 6/0036 |
| 9,766,398 | B2 * | 9/2017 | Kong | G02B 6/124 |
| 2002/0008215 | A1 * | 1/2002 | Evans | B82Y 20/00 250/559.13 |
| 2004/0156589 | A1 * | 8/2004 | Gunn, III | G02B 6/12004 385/37 |
| 2004/0156590 | A1 | 8/2004 | Gunn, III et al. | |
| 2004/0184156 | A1 * | 9/2004 | Gunn, III | G02B 6/1228 359/629 |
| 2015/0123017 | A1 * | 5/2015 | Yu | G02B 6/12007 250/503.1 |
| 2015/0268399 | A1 * | 9/2015 | Futterer | G02B 6/005 315/151 |
| 2017/0207600 | A1 * | 7/2017 | Klamkin | H01S 5/02292 |
| 2017/0351034 | A1 * | 12/2017 | Vercruysse | G02B 6/34 |
| 2017/0351035 | A1 * | 12/2017 | Rottenberg | G02B 6/124 |

FOREIGN PATENT DOCUMENTS

| | | | |
|---|---|---|---|
| WO | 2014/064228 A1 | 5/2014 | |
| WO | WO 2016107849 A1 * | 7/2016 | ............... G02B 6/34 |

* cited by examiner

LIGHT COUPLER WITH MICROSTRUCTURES ASYMMETRICALLY DISTRIBUTED ALONG LONGITUDINAL AXIS

CROSS-REFERENCE TO RELATED APPLICATION

The present application is a national stage entry of PCT/EP2015/081304 filed Dec. 28, 2015, which claims priority to EP 14200427.4 filed on Dec. 29, 2014, the contents of each of which are hereby incorporated by reference.

FIELD OF THE DISCLOSURE

The present disclosure relates to the field of integrated photonic devices. More specifically it relates to a light coupler device and a method for coupling light in and/or out an integrated photonic circuit device.

BACKGROUND

Guided-mode resonance is a phenomenon wherein the guided modes of an optical waveguide can be excited and simultaneously extracted by the introduction of a phase-matching element, such as a diffraction grating or prism.

Grating couplers are known in the art. Such coupler may comprise a diffraction grating in a region on top of or below a waveguide, e.g. an integrated waveguide in a photonic integrated circuit that may for example be composed of a transparent dielectric. Thus, off-resonance light incident on the grating may behave almost the same as it would if it was incident in an area where there is no grating, while for specific combinations of incident angles and light frequency, resonance occurs, allowing the grating to couple light into a guided mode of the waveguide.

SUMMARY

Some embodiments of the present disclosure provide efficient coupling of light into and/or out of an integrated photonic circuit device.

The above is accomplished by a method and device according to example embodiments.

In a first aspect, the present disclosure relates to a light coupler for optically coupling to an integrated waveguide, and for out-coupling a light signal propagating in the integrated waveguide into a free propagation region such as free space, e.g. a free-in-air light propagation region. The light coupler comprises a plurality of microstructures. The plurality of microstructures is adapted in shape and position to compensate decay of the light signal when propagating in the light coupler and to provide a power distribution of the light signal when coupled into free space such that the power distribution corresponds to a predetermined target power distribution, e.g. a Gaussian power distribution. Furthermore, each of the microstructures forms an optical scattering center, and the microstructures are positioned on the light coupler in accordance with a non-uniform number density function, e.g. a non-uniform two-dimensional area number density, e.g. a non-uniform number of microstructures per unit of area, e.g. per unit of area over a surface of the light coupler.

In a light coupler according to example embodiments, the non-uniform number density distribution may be a discrete sampling approximation of a continuous density distribution adapted for providing the predetermined target power distribution.

A light coupler according to example embodiments may be part of the integrated waveguide. Alternatively worded, the light coupled may comprise at least a part of the integrated waveguide, for instance a section of a wall thereof.

In a light coupler according to example embodiments, the plurality of microstructures may be at least partly fabricated in the integrated waveguide.

In a light coupler according to example embodiments, the plurality of microstructures may comprise through-holes in the integrated waveguide.

In a light coupler according to example embodiments, the plurality of microstructures may be at least partly fabricated on top of the integrated waveguide. For example, the microstructures may be sticking out of the integrated waveguide, e.g. they may, at least partly, be fabricated by depositing material, for instance metal, on the integrated waveguide.

In a light coupler according to example embodiments, the microstructures may comprise studs or pillars, shallow etched holes, deep etched holes, e.g. through holes, or other individually strongly localized features.

In a light coupler according to example embodiments, the light coupler may comprise grating lines, and the plurality of microstructures may be provided on these grating lines. For example, the grating lines may be etched into the integrated waveguide. The microstructures may be provided on the grating lines in accordance with a density distribution adapted for locally controlling the out-coupled light intensity. The light coupler may have microstructures positioned on the grating lines in accordance with a density distribution that is a discrete sampling approximation of a continuous density distribution adapted for, e.g. optimized for, providing a predetermined target out-coupled light power distribution.

In a light coupler according to example embodiments, the plurality of microstructures may be adapted in shape and form to provide a Gaussian power distribution of the light signal when propagating in free space.

A light coupler according to example embodiments may be adapted for focusing an out-coupled light signal into free space as a focused light beam converging in a focal spot.

In a second aspect, the present disclosure relates to a photonic integrated circuit comprising an integrated waveguide for guiding a light signal and a light coupler according to embodiments of the first aspect, wherein the light coupler is optically coupled to the integrated waveguide and is adapted for directing the light signal out of the plane of the waveguide as a light beam.

In a photonic integrated circuit according to example embodiments, the light coupler may form part of the integrated waveguide. In a photonic integrated circuit according to example embodiments, the plurality of microstructures may be at least partly fabricated in the integrated waveguide. In a photonic integrated circuit according to example embodiments, the plurality of microstructures may comprise through-holes in the integrated waveguide. In a photonic integrated circuit according to example embodiments, the plurality of microstructures may be at least partly fabricated on top of the integrated waveguide.

In a third aspect, the present disclosure relates to a three-dimensional (3D) display comprising a plurality of light couplers according to embodiments of the first aspect, wherein the plurality of light couplers is adapted such than an ensemble of focal spots generated by the plurality of light couplers forms a 3D image in free space.

In a fourth aspect, the present disclosure relates to a method for designing a light coupler. This method comprises designing a pattern of microstructures such that a light coupler comprising a plurality of microstructures in accordance with this pattern compensates the decay of a light signal when propagating in the light coupler and couples the light signal out in accordance with a predetermined target power distribution.

In a fifth aspect, the present disclosure relates to a method for manufacturing a light coupler for optically out-coupling a light signal from an integrated waveguide into free space. This method comprises determining a non-uniform number density distribution as a discrete sampling approximation of a continuous density distribution adapted for providing a predetermined target power distribution. This method also comprises a step of manufacturing a plurality of microstructures, forming optical scattering centers, in and/or on an integrated waveguide such that this plurality of microstructures is adapted in shape and position to compensate decay of a light signal when propagating in the light coupler and such as to provide the predetermined target power distribution of the light signal when propagating in free space. The step of manufacturing furthermore comprises positioning the microstructures on the light coupler in accordance with the non-uniform number density distribution.

Aspects of the present disclosure further provide the use of a light coupler according to embodiments of the first aspect of the present disclosure in a displaying system, for instance in a 3D displaying system, or in a lens-free cell sorting system.

Particular aspects are set out in the accompanying independent and dependent claims. Features from the dependent claims may be combined with features of the independent claims and with features of other dependent claims as appropriate and not merely as explicitly set out in the claims.

These and other aspects will be apparent from and elucidated with reference to the embodiment(s) described hereinafter.

Figure 1:
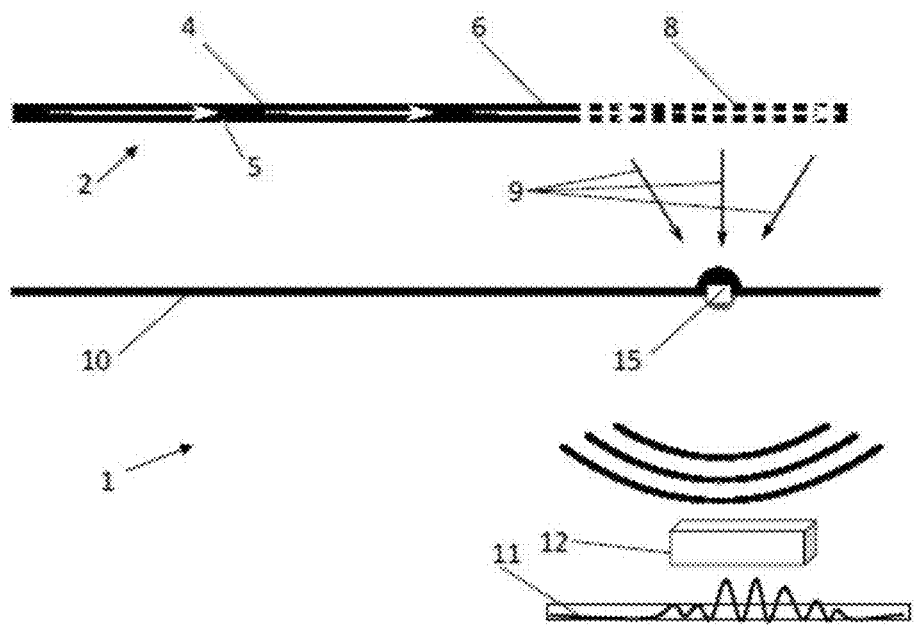
FIG. 1 illustrates an imaging device using a light coupler, according to example embodiments.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various aspects of the present disclosure. This method of disclosure, however, is not to be interpreted as reflecting an intention that the claimed subject matter requires more features than are expressly recited in each claim. Rather, as the following claims reflect, certain aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the present disclosure, and form different embodiments, as would be understood by those in the art. For example, in the following claims, any of the claimed embodiments can be used in any combination.

In the description provided herein, numerous specific details are set forth. However, it is understood that embodiments may be practiced without these specific details. In other instances, well-known methods, structures and techniques have not been shown in detail in order not to obscure an understanding of this description.

Where in embodiments reference is made to "imaging", reference is made to the process of acquiring a representation or reproduction of an object's spatial properties, e.g. the formation of a two-dimensional image. Such image may comprise a scalar value obtained for a plurality of locations, e.g. over a two-dimensional grid, for example forming a grey-scale image representation, but may also comprise a vector value for a plurality of locations, for example forming a color image representation. For example, such vector value may encode different spectral components, e.g. corresponding to recorded emission intensities for a plurality of different fluorophores. The obtained image may form a direct representation of the structure of the object, for example a magnified optical representation of a microscopic entity, but may also form a more complex representation of the structure of the object, e.g. a holographic interference pattern encoding spatial properties of the object. While imaging may relate to the recording of a static spatial representation of an object, it may also relate to the acquisition of a time series of images, e.g. the acquisition of a video sequence encoding both temporal as well as spatial variations of an optical property of the object under study.

Throughout the description, reference is made to "light". With light in the context of the present disclosure is meant electromagnetic radiation with a wavelength between 375 and 1000 nm, i.e. including visible light, IR radiation, near IR and UV radiation.

Throughout the description reference is made to "a light coupler". This refers to a light propagating region in an integrated circuit, e.g. a region in an integrated waveguide or in contact with an integrated waveguide, e.g. on top of or below an integrated waveguide, where a light dispersing structure for coupling light in and/or out of the integrated circuit is provided, such as a grating. For predetermined incident angles and light frequencies, guided mode resonance may occur, such that the grating couples light into a guided mode of the waveguide. Due to symmetry, this guided mode of the waveguide may also be coupled out of the waveguide along this predetermined angle by the coupler.

Throughout the description reference is made to "an integrated waveguide". This refers to a light propagating region integrated in or on an integrated circuit, e.g. in an integrated photonic circuit. This may refer to an optical waveguide, such as a planar waveguide, e.g. a dielectric slab waveguide, a strip waveguide, a rib waveguide, a segmented waveguide, a photonic crystal waveguide, a tapered waveguide, or any other light propagating structure known to be suitable for on-chip integration in an integrated circuit.

In a first aspect, the present disclosure relates to a light coupler for optically coupling a light signal from an integrated waveguide to a free propagating region, e.g. a region allowing substantially free propagation of the light signal, such as a free-in-air propagation region, also called free space. For example, the light coupler may be adapted for optically coupling to the integrated waveguide, and for out-coupling a light signal propagating in the integrated waveguide into a free propagation region such as free space, e.g. a free-in-air light propagation region. The light coupler comprises a plurality of microstructures, e.g. a pattern of microstructures. This plurality of microstructures is adapted in shape and position to compensate decay of the light signal when propagating in the light coupler, e.g. when the light signal is received from the integrated waveguide and propagates in the light coupler. Furthermore, the plurality of microstructures is adapted for providing a power distribution of the light signal when propagating in free space, e.g. of the out-coupled light signal, such that this power distribution corresponds to a predetermined target power distribution, e.g. to a target power distribution corresponding to a substantially planar or spherical wave, e.g. a spherical wave having a predetermined focal center. Thus, the plurality of microstructures may be adapted to provide a power distribution of the light signal when coupled into free space such that the power distribution corresponds to the predetermined target power distribution, e.g. a Gaussian power distribution. Furthermore, each of the microstructures forms an optical scattering center. The microstructures are positioned on the light coupler in accordance with a non-uniform number density function, e.g. a non-uniform two-dimensional area number density, e.g. a non-uniform number of microstructures per unit of area, e.g. per unit of area over a surface of the light coupler. For example, the pattern of microstructures may be in accordance with this density distribution, e.g. the positions of the microstructures may be sampled from such density distribution. This density distribution may be selected such that a power distribution of the light signal when coupled out of the plane of the integrated waveguide corresponds to the predetermined target power distribution. For example, in a light coupler according to example embodiments, the non-uniform number density distribution may be a discrete sampling approximation of a continuous density distribution adapted for providing the predetermined target power distribution.

In some embodiments, a light out-coupling efficiency can be achieved, e.g. giving rise to an illumination of objects. In some embodiments, the generated light cone has an increased uniformity which permits the use of larger pinholes, e.g. compared to when a conventional grating coupler is used.

Figure 2:
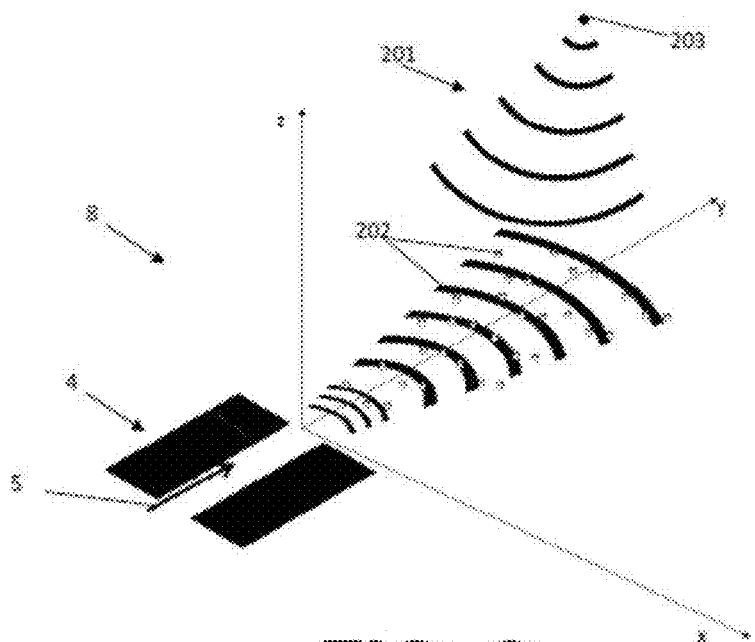
FIG. 2 illustrates a light coupler, according to example embodiments.

For example, FIG. 2 illustrates a light coupler 8 for optically coupling a light signal 5 from an integrated waveguide 4 to a free propagating region, e.g. a region allowing substantially free propagation of the light signal 5, such as a free-in-air propagation region (free space). As shown by the arrow of the light signal 5 in FIG. 2, the light signal 5 propagates along a. longitudinal axis (labeled as the y-axis) of the integrated waveguide 4 and the light coupler 8. The light coupler 8 comprises a plurality of microstructures 202, e.g. a pattern of microstructures. This plurality of microstructures 202 is adapted in shape and position to compensate decay of the light signal 5 when propagating in the light coupler 8, e.g. when the light signal is received from the integrated waveguide 4 and propagates in the light coupler 8. Furthermore, the plurality of microstructures 202 is adapted for providing a power distribution 201 of the light signal when propagating in free space, e.g. of the out-coupled light signal, such that this power distribution corresponds to a predetermined target power distribution, e.g. to a. target power distribution corresponding to a substantially planar or spherical wave, e.g. a spherical wave having a predetermined focal center 203. As shown in FIG. 2, and as further shown and explained below in connection with FIGS. 11, 12, and 16-20, the plurality of microstructures 202 can be distributed non-uniformly throughout the light coupler 8, including asymmetrically around the longitudinal axis of the integrated waveguide 4 and the light coupler 8.

A light coupler according to example embodiments may be a focusing light coupler or a defocusing light coupler, e.g. may be adapted for directing the light signal received from the integrated waveguide out of the plane of the integrated waveguide in a focused light wave, e.g. a converging light wave, or a defocused light wave, e.g. a diverging light wave. The light coupler may be a focusing light coupler for coupling light out of an integrated circuit in a focused beam, e.g. adapted for focusing the light signal out of the plane of the integrated waveguide as a focused light beam converging in a focal plane. For example, the focusing coupler may be adapted for focusing a substantially circular or planar wavefront, e.g. the light wave having a substantially circular or planar wavefront, out of the plane of the planar waveguide, e.g. out of the plane of a substrate of the photonic integrated circuit.

Figure 24:
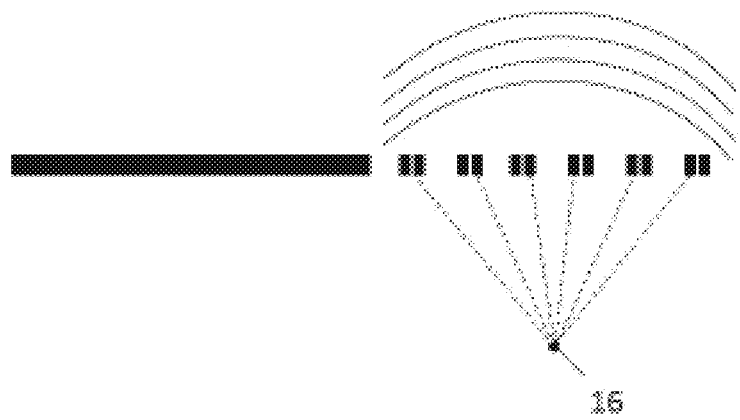
FIG. 24 illustrates a light coupler, in the form of a defocusing light coupler, according to example embodiments.

The light coupler according to embodiments may be a defocusing light coupler for coupling light out of an integrated circuit in a divergent beam, adapted for directing the light signal out of the plane of the integrated waveguide as a diverging light beam. Such an embodiment is illustrated in FIG. 24. Thus, the light coupler may be designed such that the light coupler has a virtual focal point 16 on one side of the light coupler while a light wavefront is generated on the other side of that light coupler. For example, the light coupler may comprise different structures, wherein each structure or each group of structures is designed to out-couple light to a different direction. The ensemble of structures may thus conjointly create a quasi-circular light wavefront on one side of the light coupler, e.g. on one side of the plane of the integrated waveguide, wherein the virtual focal point 16 of that wavefront is located on the other side of the grating coupler, e.g. on the opposite side of the plane of the integrated waveguide. In some embodiments, objects positioned close to the light coupler can be well illuminated, which also contributes to compactness of the device.

The light coupler according to example embodiments may comprise part of the integrated waveguide, for instance a portion of a wall thereof. For example, the light coupler may be integrally formed with the integrated waveguide, e.g. in or on an integrated photonic circuit device, such as an integrated photonic circuit according to embodiments of the second aspect of the present disclosure. For example, the integrated waveguide may comprise part of a ridge or rib waveguide, e.g. a light conducting channel defined by a slab of high refractive index material arranged between regions of low refractive index material. The light coupler may for example be provided in a slab of high refractive index material optically coupled to the ridge or rib waveguide. Alternatively, the integrated waveguide may comprise a tapered waveguide, e.g. a light conducting channel defined by a tapered region of high refractive index material arranged between regions of low refractive index material. For example, the light coupler may be formed in the tapered section of such tapered waveguide.

In a light coupler for out-coupling of a light signal, that light signal, fed by a waveguide, may decay while it propagates through the light coupler. However, in accordance with example embodiments, a plurality of microstructures is provided to compensate decay of the light signal when propagating in the light coupler. Such decay would give rise to a non-uniform distribution of light, which may for example be disadvantageous for illuminating objects in particular applications. Furthermore, the integrated waveguide may be optically coupled to different parts of the light coupler, thereby further increasing uniformity of a generated light beam. For example, the integrated waveguide may be optically coupled to one part of the light coupler and the integrated waveguide may be optically coupled to another part of the light coupler. By coupling the integrated waveguide at different locations to the light coupler, the problem of light decay inside the light coupler is solved and a light beam with uniformity can be generated. The phase difference between different light signals arriving at the light coupler, e.g. between light propagating into the coupler at the different locations, may be substantially zero, e.g. may be zero, e.g. may be as small as achievable within manufacturing tolerances and cost constraints.

The plurality of microstructures may be at least partly fabricated in the integrated waveguide. For example, the microstructures may be integrated through etching of the integrated waveguide, e.g. full etching or partly etching the integrated waveguide.

The plurality of microstructures may comprise through-holes in the integrated waveguide. For example, the cross-section of such a hole may be rectangular or have any other suitable shape, e.g. a localized shape.

The plurality of microstructures may be at least partly fabricated on top of the integrated waveguide. For example, the microstructures may be sticking out of the integrated waveguide, e.g. they may, at least partly, be fabricated by depositing material, for instance metal, on the integrated waveguide.

Thus, the pattern of microstructures may comprise studs or pillars, shallow etched holes, deep etched holes, e.g. through holes, or other individually strongly localized features.

In a light coupler according to example embodiments, the light coupler may comprise grating lines, and the plurality of microstructures may be provided on these grating lines. For example, the light coupler may comprise grating lines, e.g. etched into the integrated waveguide, whereby the pattern of microstructures may be provided on the grating lines. The microstructures may be provided on the grating lines in accordance with a density distribution adapted for locally controlling the out-coupled light intensity. The light coupler may have microstructures positioned on the grating lines in accordance with a density distribution that is a discrete sampling approximation of a continuous density distribution adapted for, e.g. optimized for, providing a predetermined target out-coupled light power distribution.

In a light coupler according to example embodiments, the plurality of microstructures may be adapted in shape and form to provide a Gaussian power distribution of the light signal when propagating in free space.

A light coupler according to example embodiments may comprise a pattern of microstructures which are fabricated, e.g. patterned, in the integrated waveguide. The microstructures may be at least partly fabricated, e.g. etched, in the waveguide. The microstructures may be through-holes in the waveguide. The through-hole may have any suitable shape, e.g. rectangular. The microstructures may also be a combination of different types of microstructures which are fabricated into the waveguide, for example microstructures which are fully (e.g. a through-hole) or partly (e.g. an indentation) fabricated into the waveguide. The pattern may be a regular pattern. According to example embodiments, the pattern may be configured to compensate for a decay of the light signal as the light signal propagates through the grating coupler when being received from the waveguide. This configured pattern ensures that the generated light cone has an increased uniformity which permits the use of larger pinholes compared to when regular patterns are used. In some embodiments, the energy of light used to illuminate objects is increased giving rise to better illumination of objects.

For example, in order to provide a uniform out-coupling of light, the microstructures may form scattering centers, e.g. the microstructures may comprise, or consist of, optical scattering centers. Thus, instead of using a fully formed focusing grating coupler that comprises a plurality of curved grating lines, the microstructures may be provided on the grating lines, e.g. at locations substantially corresponding to locations on the grating lines of a fully formed focusing grating coupler with substantially identical light coupling properties as the light coupler at hand, in accordance with a density distribution adapted for locally controlling the out-coupled light intensity. In some embodiments, the light coupler may have microstructures positioned on the light coupler in accordance with a density distribution that is a discrete sampling approximation of a continuous density distribution adapted for, e.g. optimized for, providing a predetermined target out-coupled light power distribution. In another aspect, the present disclosure may also relate to a method for designing such focusing light coupler and/or a method for manufacturing such focusing light coupler.

In a second aspect, the present disclosure also relates to a photonic integrated circuit comprising an integrated waveguide for guiding a light signal and a light coupler according to embodiments of the first aspect of the present disclosure, wherein the light coupler is optically coupled to the integrated waveguide and is adapted for directing the light signal out of the plane of the waveguide as a light beam.

In a photonic integrated circuit according to example embodiments, the light coupler may form part of the integrated waveguide. In a photonic integrated circuit according to example embodiments, the plurality of microstructures may be at least partly fabricated in the integrated waveguide. In a photonic integrated circuit according to example embodiments, the plurality of microstructures may comprise through-holes in the integrated waveguide. In a photonic integrated circuit according to example embodiments, the plurality of microstructures may be at least partly fabricated on top of the integrated waveguide.

For example, FIG. 1 shows a photonic integrated circuit 2, according to example embodiments, that comprises an integrated waveguide 4 for guiding a light signal 5. For example, the photonics integrated circuit device 2 may comprise a substrate suitable for integrated photonic circuit processing, e.g. a silicon-on-insulator (SOI) substrate, in or on which the integrated waveguide 4 is provided. In some embodiments, a light source, e.g. providing a focused light beam having a point-like focus, can be provided using integrated photonic processing technology. In some embodiments, a plurality, e.g. a large number, of such light sources can be provided on a single substrate, thus providing a low-cost and efficient to manufacture lighting source, e.g. for parallel imaging of a plurality of objects.

A photonic integrated circuit according to example embodiments may further comprise a propagation region optically coupled to the integrated waveguide 4. The propagation region may be adapted such that a large, e.g. circular, wavefront is generated in the propagation region, from a light signal 5 propagating in the waveguide 4. The propagation region may be a large surface optically coupled to the integrated waveguide 4. In some embodiments, the material of the propagation region may have the same refractive index as the refractive index of the planar waveguide 4. The free propagation region may be a slab fabricated from the same material as the integrated waveguide 4. In such an embodiment, the light coupler 8 according to example embodiments, e.g. in the form of a focusing light coupler, may be positioned in the free propagation region 14 such that the generated wavefront in the free propagation region can be coupled out of the free propagation region using the light coupler 8. For example, the light coupler 8 may be etched in the free propagation region. In some embodiments, by using such propagation region, optimized illumination of the light coupler 8 can be achieved, thereby contributing to efficient out-coupling of light by the light coupler 8.

The photonic integrated circuit 2 may further comprise an optical taper 6 optically coupled to the integrated waveguide 4 and adapted for generating a widened wavefront 7 from the light excitation signal 5. The optical taper may create an in plane two-dimensional spherical wavefront. For example a portion of the waveguide may be adapted in shape to form a tapered section for transmitting the light signal as a light wave having a substantially circular wavefront into the light coupler 8 according to example embodiments, e.g. in the form of a focusing light coupler.

Alternatively, the optical taper may be adapted for generating a substantially quasi-planar wavefront, e.g. a planar wavefront, from the light signal 5. The optical taper may create an in plane two-dimensional wavefront. For example a portion of the waveguide may be adapted in shape to form a tapered section for transmitting the light signal as a light wave having a substantially planar wavefront into the light coupler 8.

In some embodiments, the integrated waveguide may be optically coupled to a first and a second waveguide. Thus, a light signal propagating in the integrated waveguide will optically split and propagate through the first and the second waveguide. The first waveguide may be optically coupled to one side, e.g. one end, of the light coupler, and the second waveguide may be optically coupled to another side, e.g. the other end, of the same light coupler. By splitting the integrated waveguide into two waveguides, the same light signal propagating through the waveguide can be fed twice to the light coupler at different locations to compensate for, or at least reduce the effect of, decay of the light signal in the light coupler. In some embodiments, the phase difference between both light signals arriving at the light coupler is substantially zero. Thus the first and the second waveguide may be fabricated such that that the phase difference between light signals arriving at the light coupler is substantially zero, e.g. is equal to zero, e.g. is equal to zero within a predetermined tolerance range, e.g. within manufacturing tolerances.

In some embodiments, the integrated waveguide may be optically coupled to the light coupler at a plurality of locations of the light coupler for increasing uniformness of the light beam even further. For example, the integrated waveguide may be optically coupled to a plurality of waveguides, e.g. to three, four, five, six or even more waveguides. Thus, a light signal propagating in the integrated waveguide will optically split and propagate through each of this plurality of waveguides. The plurality of waveguides may be optically coupled to a plurality of locations on the grating coupler.

The focusing light coupler may be adapted for focusing the substantially circular or planar wavefront 7 out of the plane of the waveguide as a focused light beam 9 converging in a focal plane 10.

Figure 3:
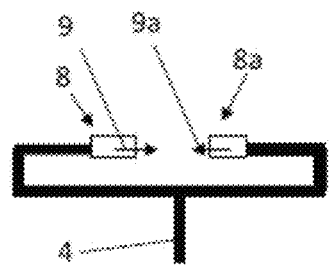
FIG. 3 illustrates an imaging device using a light coupler, according to example embodiments.
Figure 4:
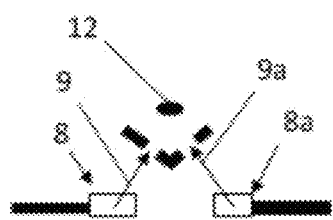
FIG. 4 illustrates an imaging device using a light coupler, according to example embodiments.

Different light couplers may for example be used to simultaneously illuminate an object from different angles. The different light couplers may be connected to the same integrated waveguide which provides the light signal to all the light couplers. For example, the integrated circuit 2 may comprise at least one further light coupler 8a according to example embodiments, which is optically coupled to the waveguide 4. The at least one further light coupler 8a may be adapted for directing the light signal 5 out of the plane of the integrated waveguide 4 as a light beam 9a. The light coupler 8 and the at least one further light coupler 8a are positioned such that generated light beams by the light coupler 8 and the at least one further light coupler 8a coincide and thereby simultaneously illuminate the object from different angles. Such embodiments are illustrated in FIG. 3 and FIG. 4. For example, illumination of an object from different angles allows the recording of 3D information of the object. Thus, by incorporating the 3D information to identify the object, a higher accuracy can be achieved.

In a photonic circuit comprising a plurality of light couplers according to example embodiments, each light coupler may have its own integrated waveguide that feeds a light signal into that light coupler and the different light couplers may be positioned to illuminate an object from different angles. For example, the photonic integrated circuit may comprise a first integrated waveguide and a second integrated waveguide for guiding a light signal (the present disclosure, however, not being limited to only two waveguides), and a first light coupler optically coupled to the first integrated waveguide and a second light coupler optically coupled to the second integrated waveguide (the present disclosure neither being limited to only two light couplers). The second light coupler may be adapted for directing the light signal out of the plane of the second waveguide as another light beam. The first light coupler and the second light coupler may be positioned such that generated light beams by the first and second light couplers coincide and thereby simultaneously illuminate the object from different angles.

In a third aspect, the present disclosure also relates to a method for designing a light coupler. This method comprises designing a pattern of microstructures such that a light coupler comprising a plurality of microstructures in accordance with this pattern compensates the decay of a light signal when propagating in the light coupler and couples the light signal out in accordance with a predetermined target power distribution, e.g. can out-couple the light signal such that it corresponds to a predetermined target power distribution.

In a fourth aspect, the present disclosure relates to a method for manufacturing a light coupler for optically coupling, e.g. for optically out-coupling, a light signal from an integrated waveguide to a free propagation region, e.g. a region allowing substantially free propagation of the light signal, such as a free-in-air propagation region, e.g. for optically out-coupling the light signal from the integrated waveguide into free space. This method comprises determining a non-uniform number density distribution as a discrete sampling approximation of a continuous density distribution adapted for providing a predetermined target power distribution e.g. a target power distribution corresponding to a substantially planar or spherical wave, e.g. a spherical wave having a predetermined focal center. This method comprises a step of manufacturing a plurality of microstructures, forming optical scattering centers, in and/or on an integrated waveguide such that this plurality of microstructures is adapted in shape and position to compensate decay of a light signal when propagating in the light coupler, e.g. when received from the integrated waveguide, and such as to provide the predetermined target power distribution of the light signal when propagating in free space, e.g. of the out-coupled light signal. The step of manufacturing furthermore comprises positioning the microstructures on the light coupler in accordance with the non-uniform number density distribution.

For example, the pattern of microstructures may be in accordance with a density distribution, e.g. the positions of the microstructures may be sampled from such density distribution. This density distribution may be selected such that a power distribution of the light signal when coupled out of the plane of the integrated waveguide corresponds to the predetermined target power distribution.

Figure 5:
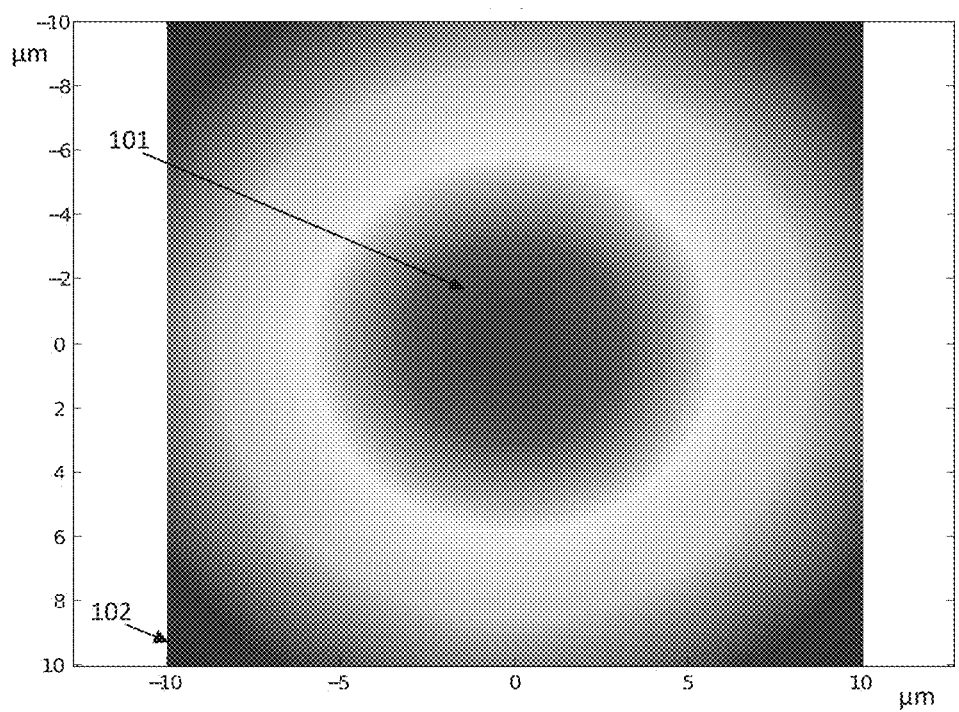
FIG. 5 shows an out-coupling power distribution for providing an approximation of a point source, for illustrating aspects of example embodiments.

Referring to FIG. 5, an out-coupling power distribution R is shown that could provide an approximation of a point source. For example, in a central area 101 of the plane in which the light coupler is to be formed, the out-coupled power can be lower than in a peripheral area 102, e.g. in order to account for a larger distance for the out-coupled wave to travel before reaching the focal point above the central area 101, e.g. to overcome an inverse squared distance loss factor. This out-coupling power distribution R(r) can be related to the power distribution P in the light coupler, e.g. by the mathematical model:

$$\frac{dP(r)}{dr} = -\frac{1}{r}P(r) - R(r);$$

Figure 6:
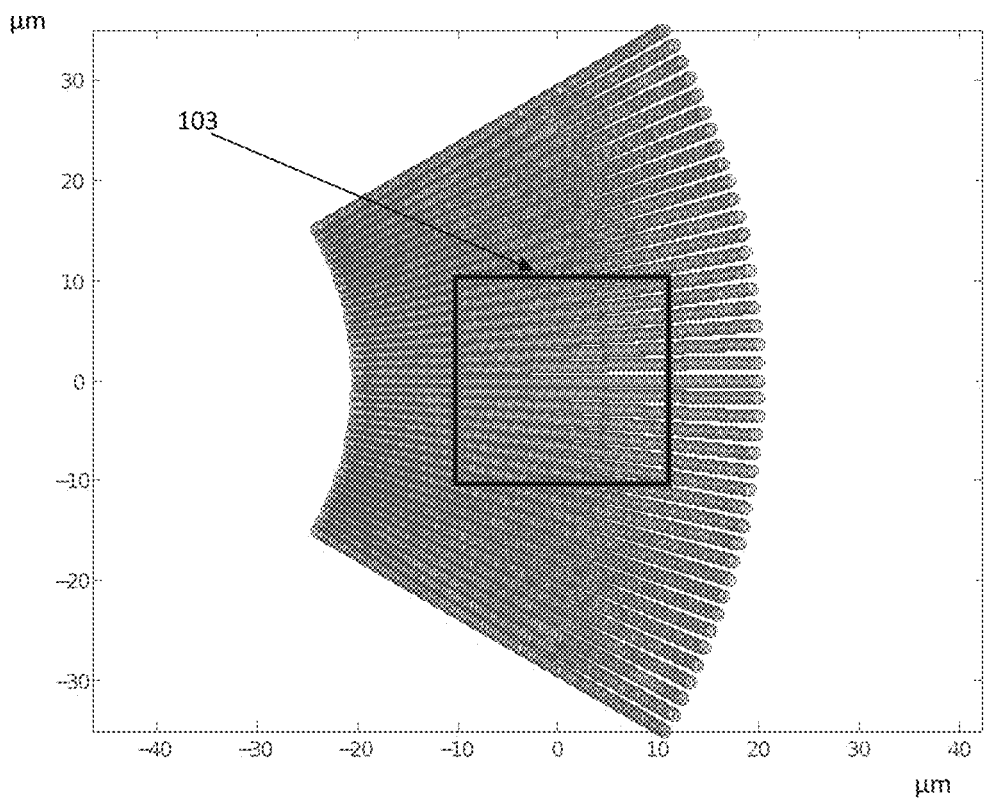
FIG. 6 shows a grating coupler, according to example embodiments.
Figure 7:
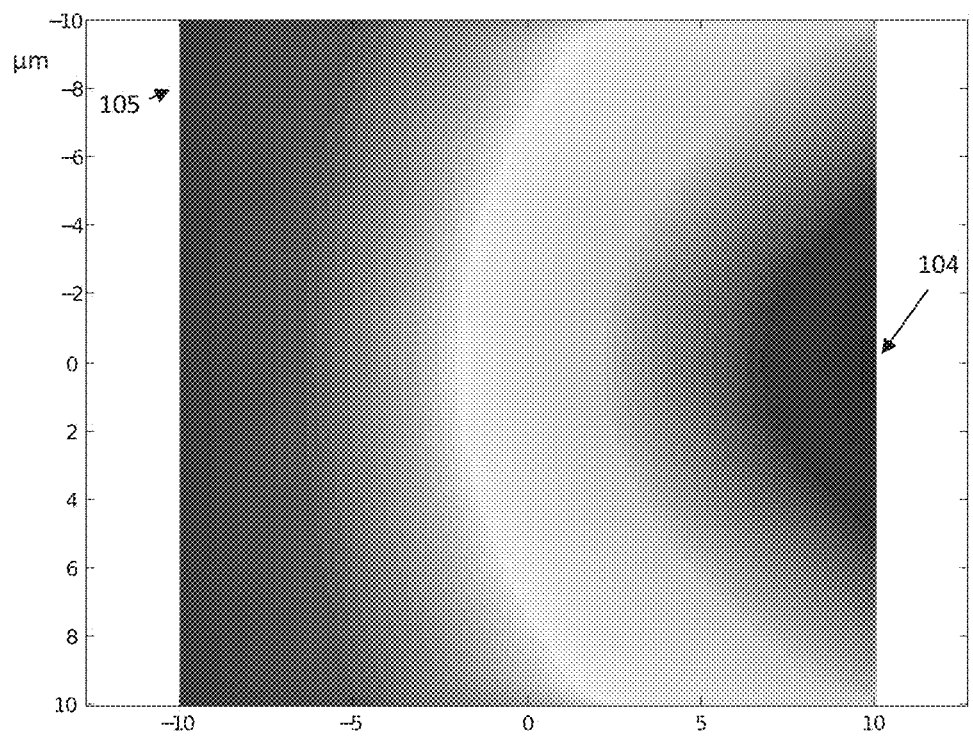
FIG. 7 shows a target power distribution of light propagating through a grating coupler, according to example embodiments.
Figure 8:
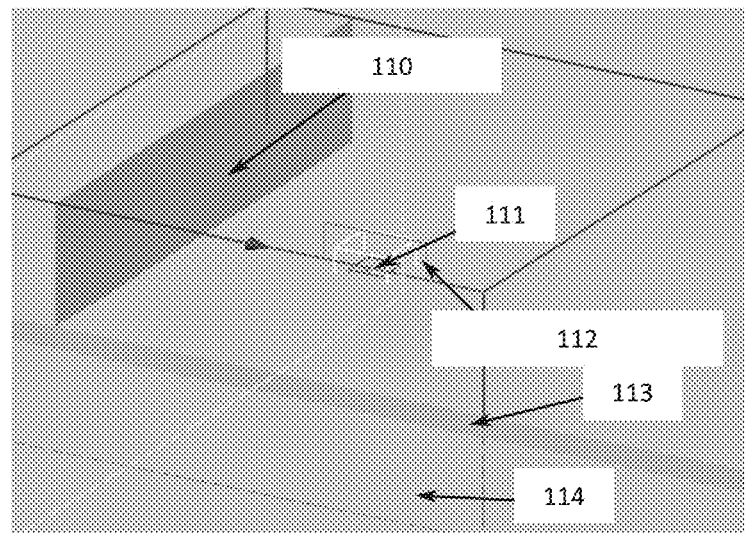
FIG. 8 shows a simulation model for determining the scattering cross-section of a microstructure for use in a light coupler, according to example embodiments.
Figure 9:
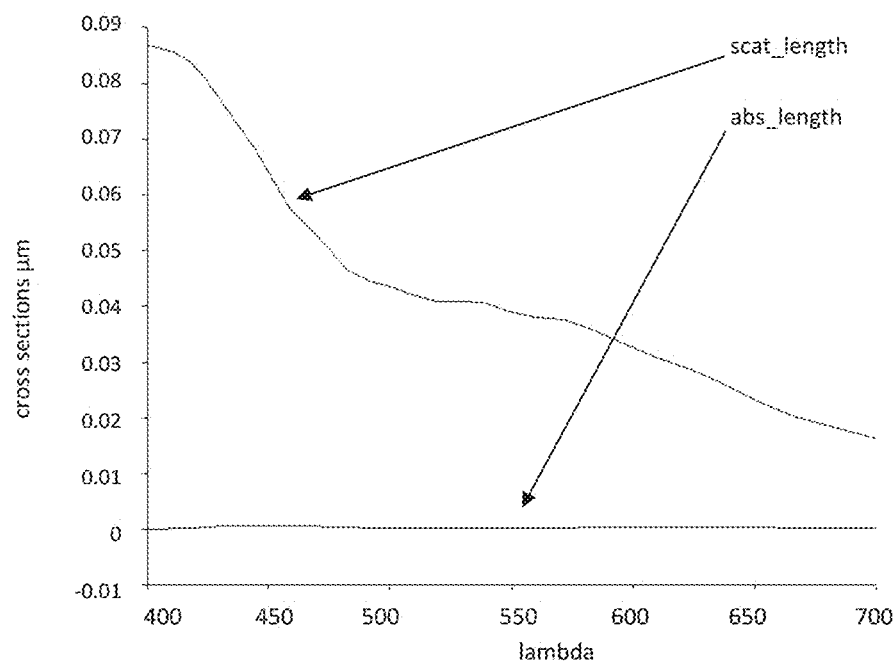
FIG. 9 shows simulated scattering cross-sections as a function of wavelength of a microstructure for use in a light coupler, according to example embodiments.

Thus, the distribution P(r) can be determined by this model for the out-coupling power distribution R shown in FIG. 5. For example, the distribution P(r) over a part 103 of a light coupler according to example embodiments, shown in FIG. 6, is illustrated in FIG. 7. Therefore, in order to obtain an out-coupled power distribution that approximates a point source, as shown in FIG. 5, a power distribution gradient P(r), ranging from high 105 to low 104, may be provided in the coupler as shown in FIG. 7. Since the out-coupling power distribution R is also related to the scattering cross-section and scatter density, as follows:

$$\frac{dP(r)}{dr} = -\frac{1}{r}P(r) - n\sigma P(r);$$

a target scatterer density n can be defined when the cross-section σ is known. This cross-section can for example be obtained by simulation, e.g. using Lumerical software. For example, FIG. 8 shows a simulation model, comprising a mode source 110 and a microstructure acting 111 as scatterer, e.g. a shallow etch. The model also comprises a field monitoring box 112 for measuring the scattering field in order to calculate the simulated scattering cross-section. The simulated model uses a SiN 113 on $SiO_2$ 114 platform. FIG. 9 shows example simulation results of the scattering cross-section σ as function of the wavelength λ.

Figure 10:
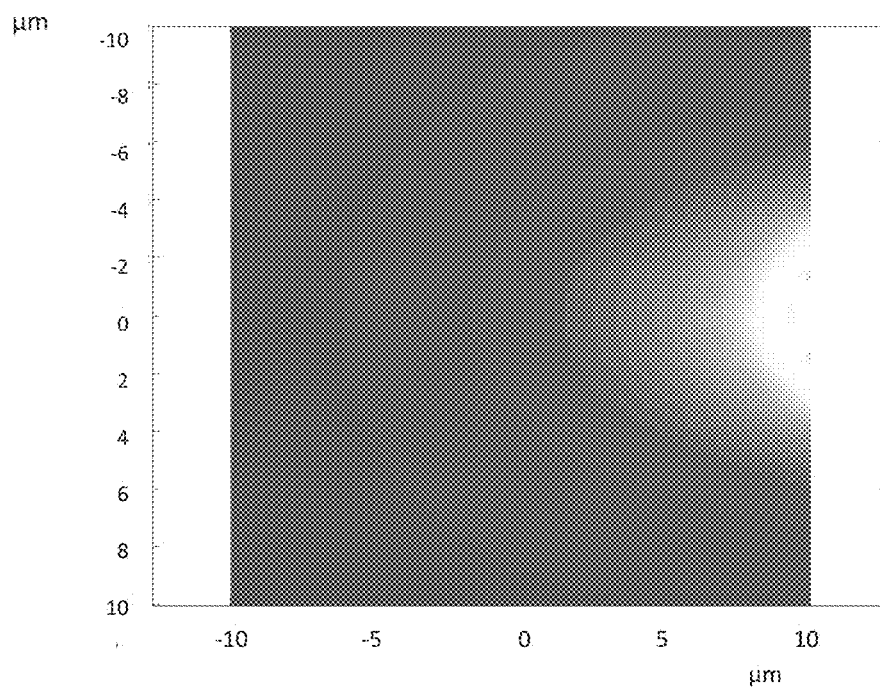
FIG. 10 shows a target distribution of scattering microstructures for use in a light coupler, according to example embodiments.
Figure 11:
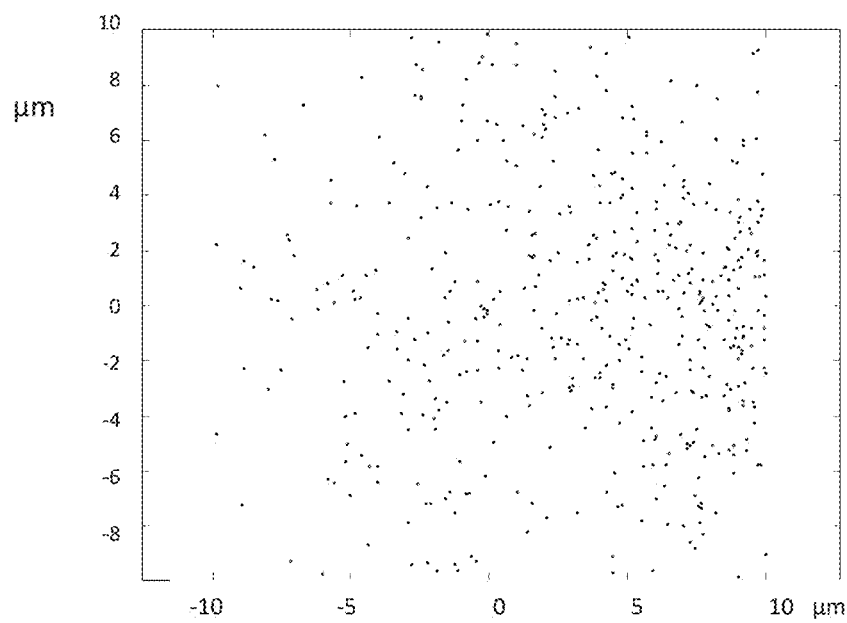
FIG. 11 shows a random sampling of scattering microstructure locations from a target distribution of scattering microstructures for use in a light coupler, according to example embodiments.
Figure 12:
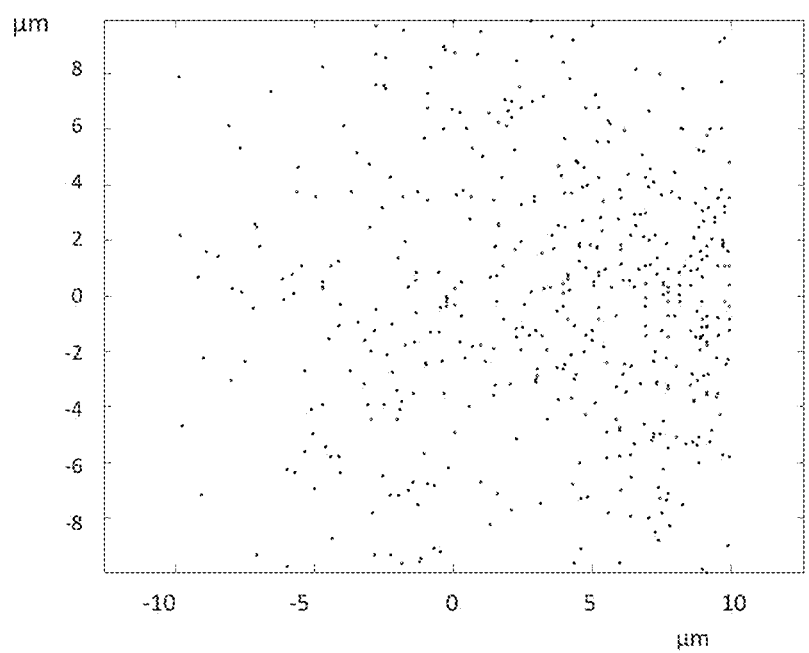
FIG. 12 shows a random sampling of scattering microstructure locations from a target distribution of scattering microstructures for use in a light coupler, wherein these randomly sampled locations are adjusted such as to fall on the nearest grating line, according to example embodiments.

FIG. 10 shows an example distribution n of scattering centers corresponding to the example simulation results shown in FIG. 9 and the target power distribution P shown in FIG. 7, in accordance with the mathematical relation hereinabove. This distribution can for example be used to randomly sample positions for the microstructures to be fabricated in the waveguide according to example embodiments, e.g. as shown in FIG. 11. Furthermore, the position of each such randomly sampled location may be adjusted such as to fall on the nearest grating line, e.g. as shown in FIG. 12.

Figure 13:
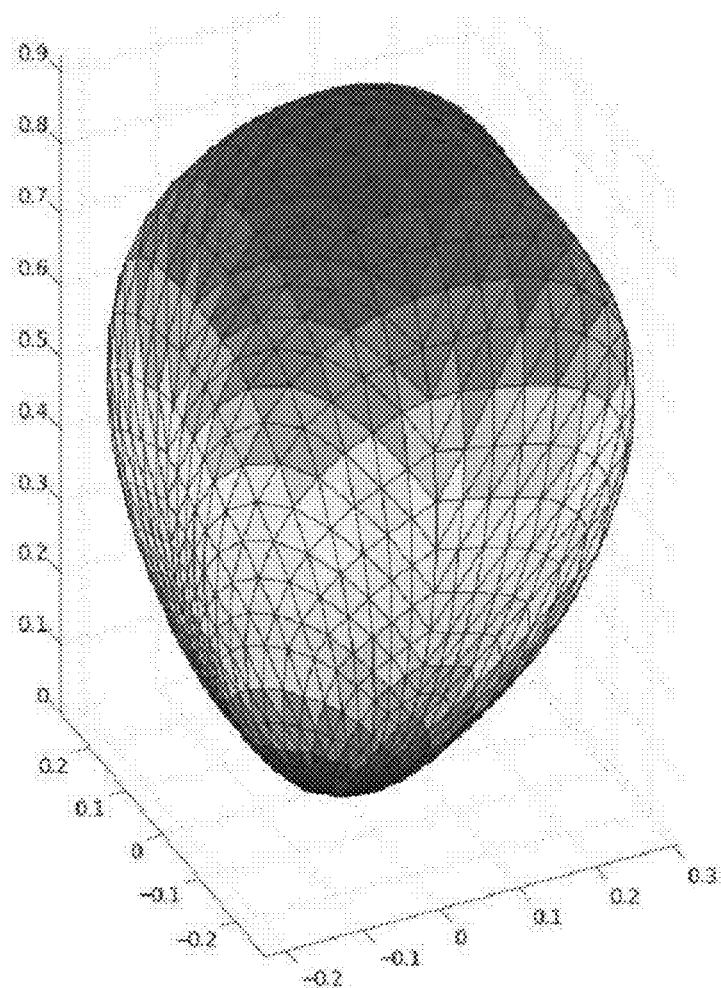
FIG. 13 shows an iso-intensity surface of scattered light obtained by a simulation of a light coupler, according to example embodiments.
Figure 14:
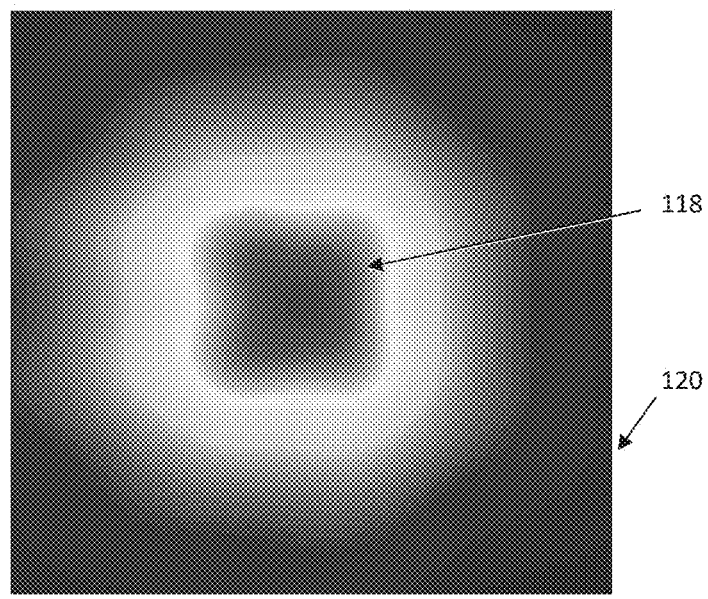
FIG. 14 shows a scattering intensity plot of a simulation of a light coupler, according to example embodiments.
Figure 15:
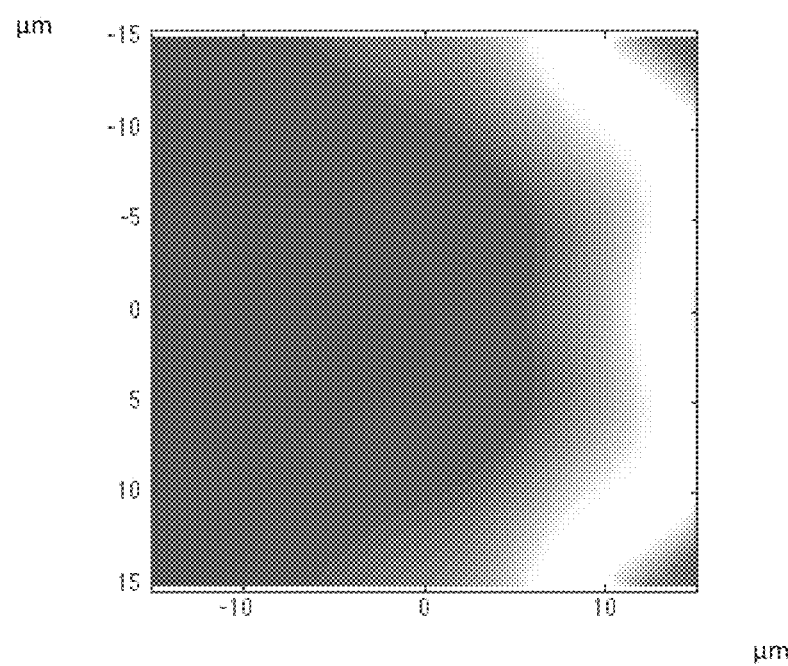
FIG. 15 shows a target distribution for scattering center locations in which anisotropy of the scattering microstructures is taken into account, according to example embodiments.
Figure 16:
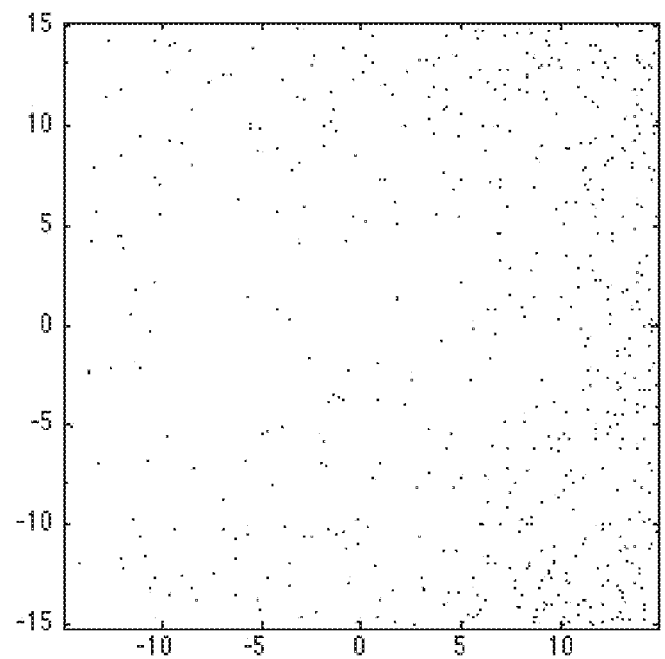
FIG. 16 shows a random sampling of microstructures in accordance with a target density distribution compensated for anisotropic scattering of the microstructures, according to example embodiments.
Figure 17:
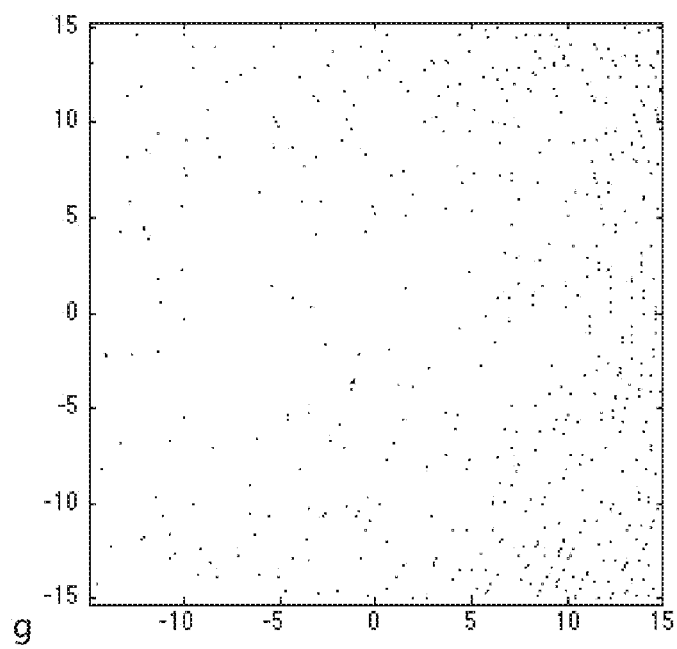
FIG. 17 shows a random sampling of microstructures in accordance with a target density distribution compensated for anisotropic scattering of the microstructures, wherein the randomly sampled microstructure locations are adjusted to the nearest position on a grating line, according to example embodiments.

Since the scatterer may be not isotropic, anisotropic scattering may also be taken into account. FIG. 13 shows an iso-intensity surface of scattered light obtained by a simulation. FIG. 14 shows a 2D scattering intensity plot of the same simulation, showing the decreasing intensity of scattering from a central area 118 to a peripheral area 119 of the microstructure. For example, an anisotropy induced by the rectangular shape of the modelled microstructure etch can be seen on FIG. 13 and FIG. 14. FIG. 15 shows an example distribution n for the scattering centers, after taking such anisotropy of the microstructures into account. FIG. 16 and FIG. 17 show respectively a random sampling of microstructures in accordance with this distribution n compensated for the anisotropic scattering of the microstructures, and these randomly sampled microstructure locations adjusted to the nearest position on a grating line.

Figure 18:
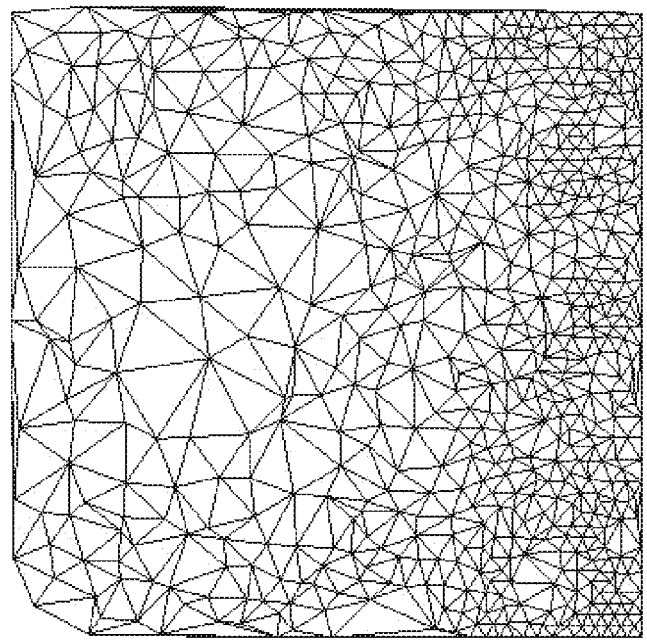
FIG. 18 illustrates a mesh for iteratively improving the conformity of a simulated light coupler, according to example embodiments.
Figure 19:
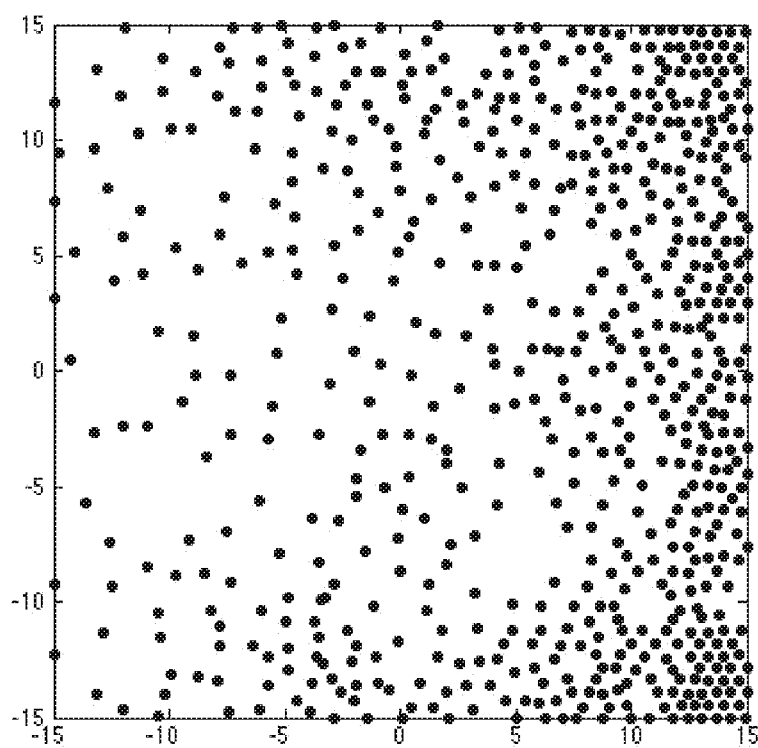
FIG. 19 shows a first positioning of scattering microstructures in a simulated light coupler, corresponding to an iteration in a iterative mesh optimization simulation, according to example embodiments.
Figure 20:
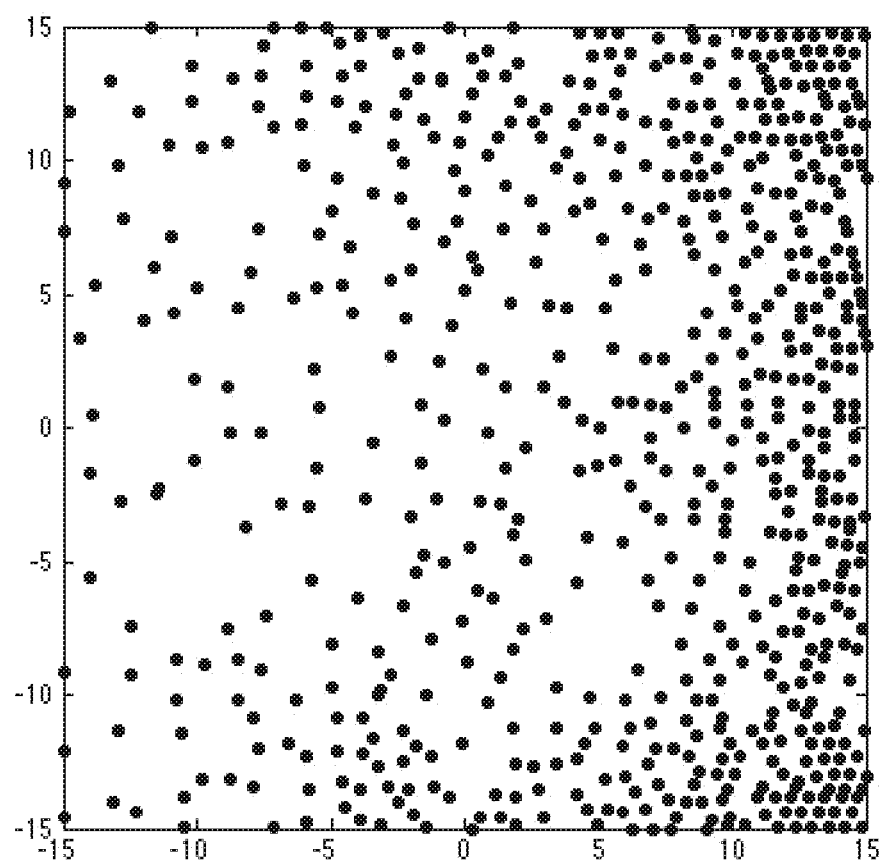
FIG. 20 shows a second positioning of scattering microstructures in a simulated light coupler, corresponding to another iteration in an iterative mesh optimization simulation, according to example embodiments.

Furthermore, the conformity of the grating coupler for providing an approximated point source may be further improved by using meshing tools, e.g. to adjust the spacing between microstructure locations, for example obtained by an initial random sampling as discussed hereinabove, so as to improve a simulated out-coupled field conformity to the target point source distribution in each iteration. FIG. 18 illustrates such mesh, while FIG. 19 and FIG. 20 illustrate the microstructure positioning in two mesh correction iterations.

Figure 21:
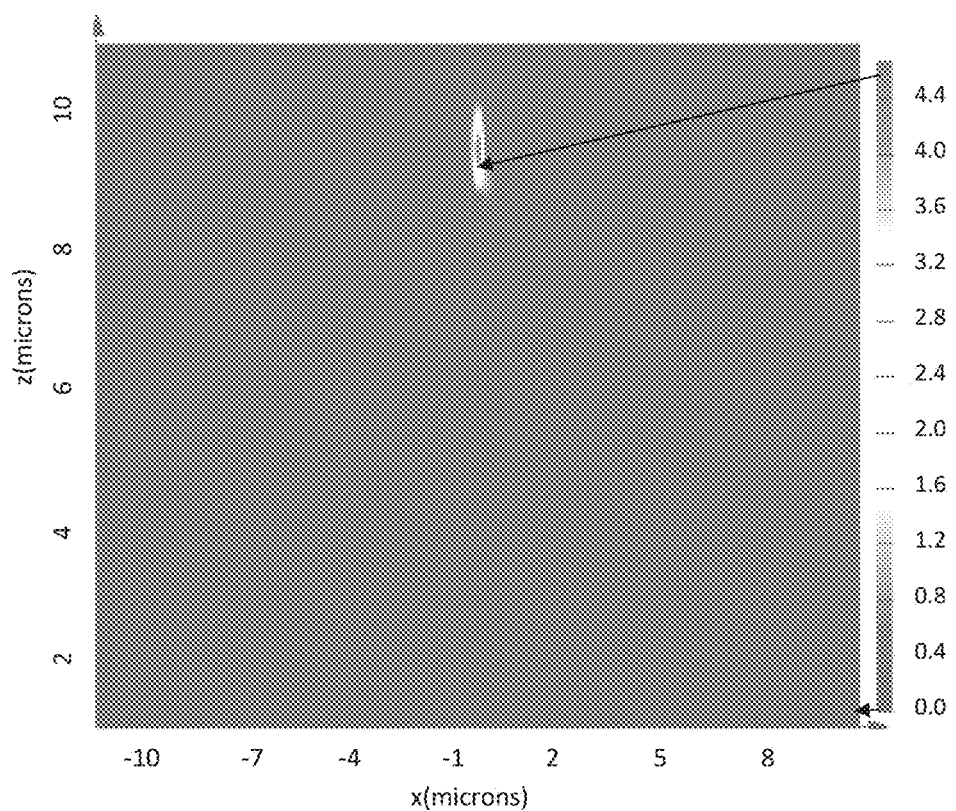
FIG. 21 shows a simulated out-coupled light field of a light coupler, illustrating the focal spot formed at a focal distance above the plane of the coupler, according to example embodiments.
Figure 22:
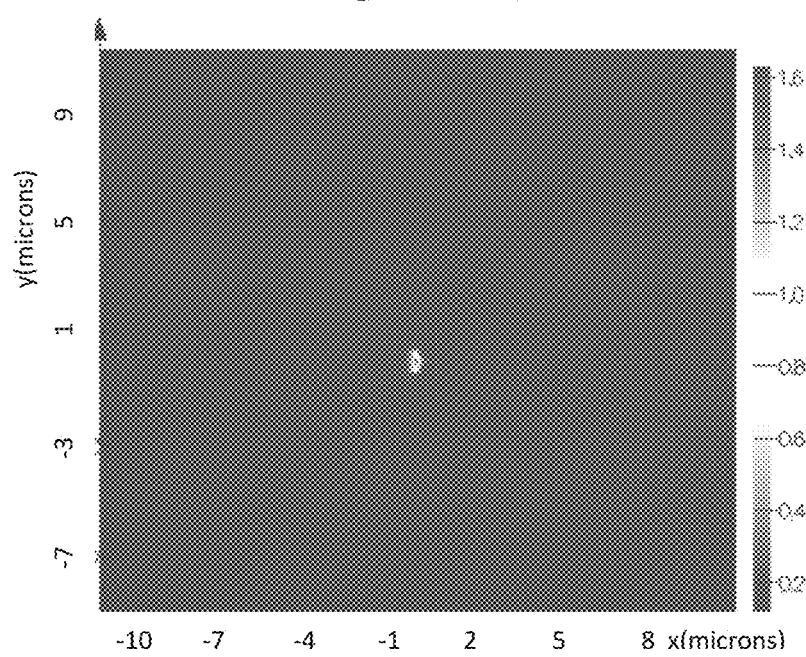
FIG. 22 shows a simulated out-coupled light field of a light coupler, illustrating the focal spot in a focal plane parallel to the plane of the coupler, according to example embodiments.
Figure 23:
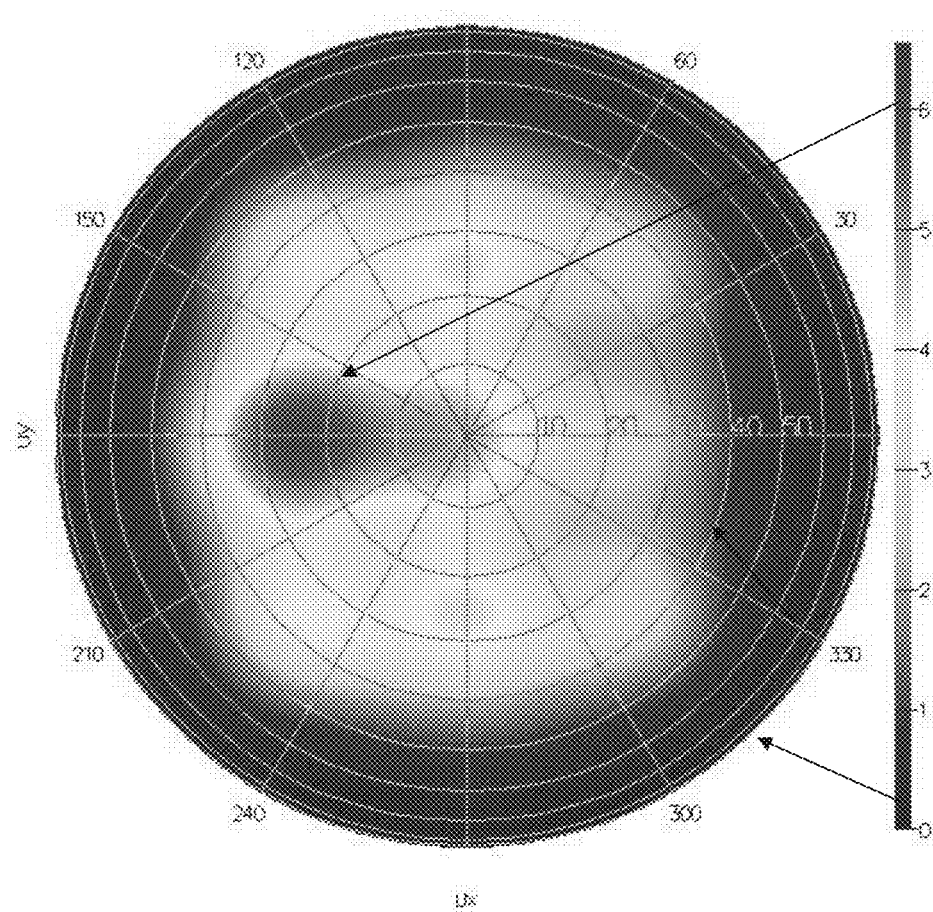
FIG. 23 shows the far field of out-coupled light of a simulated light coupler, according to example embodiments.

FIGS. 21 to 23 show a simulated field above a light coupler that comprises microstructures as obtained by a procedure described hereinabove. The simulated coupler has dimensions 10 μm by 10 μm in the z=0 plane of the simulation coordinate system. The coupler was designed to provide a focus at a distance of 10 μm, at (x,y,z)=(0,0,10) μm. FIG. 21 shows the focal spot formed at this distance above the coordinate system origin. FIG. 22 shows the focal spot of about 250 nm formed in the focal plane. FIG. 23 shows the far field of the light coupled out of the waveguide by the grating coupler.

For example, a light coupler according to example embodiments may be particularly suitable for use in an imaging device. For example, such imaging device, e.g. a lens-free imaging device, may comprise at least one photonic integrated circuit according to example embodiments of the second aspect. This at least one photonic integrated circuit comprises an integrated waveguide for guiding a light signal and a light coupler according to example embodiments, optically coupled to the integrated waveguide and adapted for directing the light signal out of a plane of the integrated waveguide as a light beam. The imaging device may further comprise at least one imaging detector positioned for imaging an object illuminated by the light beam. This object may for example comprise a fluid, e.g. a fluid comprising an immersed biological sample. The imaging device may comprise a microfluidic channel for containing the object to be imaged, e.g. to contain a fluid medium to be analyzed.

Referring to FIG. 1, an imaging device 1 comprising a light coupler, according to example embodiments, is shown. Particularly, the imaging device 1 may be a lens-free imaging device, e.g. a device for obtaining a spatial representation of an object by observing a spatial pattern obtained by attenuation, reflection, refraction, diffraction, and/or phase modulation of a light wave incident on the object without requiring an optical lens structure. The lens-free imaging device may be a lens-free cell sorting device having a plurality of light couplers and micro-fluidic channels wherein light couplers illuminate objects propagating in the micro-fluidic channels. For example, each micro-fluidic channel may comprise a light coupler for illuminating objects. The device may for example be adapted for imaging the object under magnification, e.g. for obtaining an image of an object under magnification, such as microscopic imaging. This imaging device 1 comprises at least one photonic integrated circuit 2 according to embodiments of the second aspect.

For example, the imaging device 1 may comprise a light source, e.g. an at least partially coherent light source, for providing a light signal 5 to the at least one photonic integrated circuit 2. For example, such light source may comprise a laser or light-emitting diode (LED) to provide at least partially coherent light with a limited bandwidth for coupling to the integrated waveguide on the photonic integrated circuit. In some embodiments, for example, holographic imaging can be provided of an object in an efficient and low-cost manner, e.g. holographic imaging of a large number of objects simultaneously.

The imaging device 1 further comprises at least one imaging detector 11, such as a CMOS image detector, positioned for imaging an object 12 illuminated by the light beam 9. The at least one imaging detector 11 may for example be adapted for imaging the object when the object is positioned downstream of a focal plane with respect to the propagation direction of the light beam, in embodiments where the generated light beam is a focused light beam. Furthermore, the imaging device may comprise other parts for performing image acquisition, digitization and/or transmission, and/or storage of the image. The imaging device may also comprise processing means, e.g. a processor such as an application specific integrated circuit device, adapted for performing image processing operations, such as for example image filtering, image transformation, pattern recognition and/or image compression.

The object 12 may for example comprise a fluid, e.g. a fluid comprising an immersed biological sample, contained in a microfluidic channel.

The at least one imaging detector may for example be adapted for acquiring a holographic diffraction image of the object 12 and/or may be adapted for acquiring a fluorescence image of the object 12.

The device may comprise at least one pinhole 15, positioned in between the photonic integrated circuit 2 and the at least one imaging detector 11 for spatially filtering the light beam 9, e.g. for filtering the light beam before reaching the object. For example, the wavefront of a focused light beam may be cleaned up by a pinhole at the focal plane, e.g. the pinhole collimator may implement a low spatial frequency band pass filter. The at least one pinhole collimator may thus be positioned in the focal plane for spatially filtering the focused light beam.

The at least one imaging detector 11 may be adapted for simultaneously imaging a plurality of objects 12, wherein each object of the plurality of objects is positioned such as to allow illumination of each object by a corresponding light beam emitted by a corresponding light coupler according to example embodiments, e.g. when each object is positioned downstream of the focal plane with respect to the propagation direction of a corresponding focused beam emitted by a corresponding light coupler. An imaging device comprising a light coupler according to embodiments may also comprise a reflective surface, wherein the reflective surface and the at least one imaging detector are positioned such that light from the illuminated object and the light beam is reflected by the reflective surface and detected by the at least one imaging detector after reflection.

In an aspect of the disclosure, the light coupler may be used in a displaying system. The displaying system may be a 3D displaying system such as a holographic displaying system. Such a system may comprise a plurality of light couplers wherein each light coupler is a focusing light coupler as described above. The system may comprise a plurality of waveguides, each waveguide being optically coupled to a light coupler. Each light coupler may be designed such that the light signal fed by the waveguide is out-coupled into a focal light spot in free space. Further, the plurality of light couplers may be adapted such that the ensemble of focal light spots of different light couplers forms a virtual 3D object in free space, e.g. a holographic object. For example, each light coupler may redirect light into a different direction such that each light coupler generates a focal spot at a different location in free space.

Figure 25:
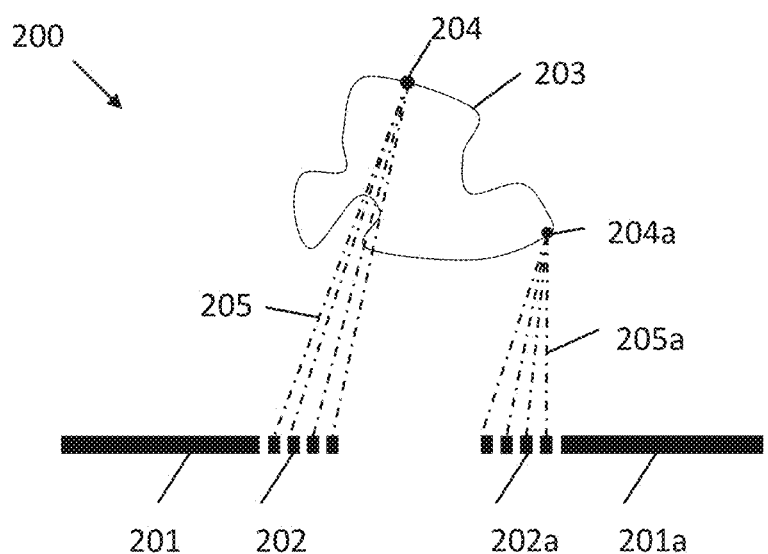
FIG. 25 illustrates a displaying system, according to example embodiments.

FIG. 25 illustrates an embodiment of such a displaying system. The system comprises a plurality of optical waveguides 201, 201a. Each optical waveguide 201, 201a is optically coupled to at least one light coupler 202, 202a, respectively. A light signal fed into the optical waveguide 201, 201a is propagated towards the light coupler 202, 202a. The light coupler is adapted such that the light signal is coupled out of the optical waveguide as a focused light beam 205, 205a having a focal light spot 204, 204a in free space. The plurality of light couplers 202, 202a is adapted such that the ensemble of focal light spots 204, 204a creates a virtual 3D object 203 in the free space, e.g. a holographic object.

The invention claimed is:

1. A light coupler for out-coupling a light signal propagating in an integrated waveguide into free space, the light coupler comprising:
   a plurality of microstructures including one or more of (i) pillars on a surface of the light coupler or (ii) holes etched into the surface, wherein the light coupler defines a longitudinal axis in a direction of propagation of the light signal into the light coupler,
   wherein the plurality of microstructures is adapted in shape and position to:
      compensate decay of the light signal when propagating in the light coupler; and
      provide a target power distribution of the light signal when coupled into free space,
   wherein the target power distribution corresponds to a substantially planar or spherical wave,
   wherein each microstructure of the plurality respectively forms an optical scattering center, and
   wherein the plurality of microstructures are positioned on the surface in accordance with a non-uniform distribution adapted for providing the target power distribution, and wherein the non-uniform distribution comprises at least some of the microstructures of the plurality of microstructures being asymmetrically distributed around the longitudinal axis.

2. The light coupler according to claim 1, wherein the non-uniform distribution is a discrete sampling approximation of a continuous density distribution adapted for providing the target power distribution.

3. The light coupler according to claim 1,
   wherein the light coupler comprises grating lines, and
   wherein the plurality of microstructures extend from the grating lines.

4. The light coupler according to claim 1, wherein the plurality of microstructures being adapted in shape and position to provide the target power distribution comprises the plurality of microstructures being adapted in shape and form to provide a Gaussian power distribution of the light signal when propagating in free space.

5. The light coupler according to claim 1, wherein the light coupler is adapted for focusing an out-coupled light signal into free space as a focused light beam converging in a focal spot.

6. The light coupler according to claim 5,
wherein the light coupler is a component, along with other similar light couplers forming a plurality of light couplers, of a three-dimensional (3D) display, and
wherein the plurality of light couplers is adapted such that an ensemble of focal spots generated by the plurality of light couplers forms a three-dimensional image in free space.

7. The light coupler according to claim 1, wherein the light coupler is a component of a displaying system.

8. The light coupler according to claim 1, wherein the light coupler is a component of a three-dimensional (3D) displaying system.

9. The light coupler according to claim 1, wherein the light coupler is a component of a lens-free cell sorting system.

10. A photonic integrated circuit comprising:
an integrated waveguide for guiding a light signal; and
a light coupler for out-coupling a light signal propagating in the integrated waveguide into free space, the light coupler comprising:
a plurality of microstructures including one or more of (i) pillars on a surface of the light coupler or (ii) holes etched into the surface, wherein the light coupler defines a longitudinal axis in a direction of propagation of the light signal into the light coupler,
wherein the plurality of microstructures is adapted in shape and position to:
compensate decay of the light signal when propagating in the light coupler; and
provide a target power distribution of the light signal when coupled into free space,
wherein the target power distribution corresponds to a substantially planar or spherical wave,
wherein each microstructure of the plurality respectively forms an optical scattering center,
wherein the plurality of microstructures are positioned on the surface in accordance with a non-uniform distribution adapted for providing the target power distribution, and wherein the non-uniform distribution comprises at least some of the microstructures of the plurality of microstructures being asymmetrically distributed on the surface along the first axis and at least some of the microstructures of the plurality being asymmetrically distributed around the longitudinal axis, and
wherein the light coupler is adapted for directing the light signal out of a plane of the integrated waveguide as a light beam.

11. The photonic integrated circuit according to claim 10, wherein the light coupler forms part of the integrated waveguide.

12. The photonic integrated circuit according to claim 10, wherein the plurality of microstructures is at least partly fabricated in the integrated waveguide.

13. The photonic integrated circuit according to claim 10, wherein the holes comprise through-holes in the integrated waveguide.

14. The photonic integrated circuit according to claim 10, wherein the plurality of microstructures is at least partly fabricated on top of the integrated waveguide.

15. The photonic integrated circuit according to claim 10,
wherein the light coupler comprises grating lines, and
wherein the plurality of microstructures extend from the grating lines.

16. The photonic integrated circuit according to claim 10, wherein the light coupler is adapted for focusing an out-coupled light signal into free space as a focused light beam converging in a focal spot.

17. The photonic integrated circuit according to claim 10, wherein the photonic integrated circuit is a component of a displaying system.

18. The photonic integrated circuit according to claim 10, wherein the photonic integrated circuit is a component of a three-dimensional (3D) displaying system.

19. The photonic integrated circuit according to claim 10, wherein the photonic integrated circuit is a component of a lens-free cell sorting system.

20. A method for manufacturing a light coupler for optically out-coupling a light signal from an integrated waveguide into free space, the method comprising:
determining a non-uniform distribution as a discrete sampling approximation of a continuous density distribution adapted for providing a target power distribution; and
manufacturing a plurality of microstructures forming optical scattering centers in or on the integrated waveguide such that the plurality of microstructures is adapted in shape and position to:
compensate decay of a light signal when propagating in the light coupler; and
provide the target power distribution of the light signal when coupled into free space,
wherein the target power distribution corresponds to a substantially planar or spherical wave,
wherein the plurality of microstructures include one or more of (i) pillars on a surface of the light coupler or (ii) holes etched into the surface, wherein the light coupler defines a longitudinal axis in a direction of propagation of the light signal into the light coupler, and
wherein the manufacturing comprises positioning the plurality of microstructures on the surface in accordance with the non-uniform distribution and wherein the non-uniform distribution comprises at least some of the microstructures of the plurality being asymmetrically distributed around the longitudinal axis.

* * * * *